United States Patent [19]

Kogoma et al.

[11] Patent Number: 4,579,980

[45] Date of Patent: Apr. 1, 1986

[54] PROCESS FOR PRODUCING ETHER COMPOUNDS

[75] Inventors: Kiyoshi Kogoma, Chiba; Norio Sone; Takashi Tobita, both of Ichihara; Masahiro Shiozaki, Yokohama, all of Japan

[73] Assignee: Nippon Soda Co. Ltd., Tokyo, Japan

[21] Appl. No.: 701,814

[22] Filed: Feb. 19, 1985

Related U.S. Application Data

[63] Continuation of Ser. No. 544,536, Oct. 24, 1983, abandoned.

[30] Foreign Application Priority Data

Nov. 5, 1982 [JP] Japan .............................. 57-193522

[51] Int. Cl.[4] .............................................. C07C 41/14
[52] U.S. Cl. .................................. 568/618; 568/622; 568/630; 568/594; 568/671; 568/672; 568/678; 568/679
[58] Field of Search ............... 568/594, 606, 607, 608, 568/613, 618, 630, 640, 671, 672, 678, 679

[56] References Cited

U.S. PATENT DOCUMENTS 4,385,190 5/1983 Ohashi et al.

*Primary Examiner*—Howard T. Mars
*Attorney, Agent, or Firm*—George B. Oujevolk

[57] ABSTRACT

An ether compound is advantageously produced by an ether exchange reaction of a different ether compound and a hydroxy group containing compound in the presence of a heteropoly acid or an acidic salt thereof as the catalyst. The catalyst is novel and is extremely effective to the present process and brings about less by-products compared to other processes or other catalysts.

5 Claims, No Drawings

PROCESS FOR PRODUCING ETHER COMPOUNDS

This application is a continuation of Ser. No. 544,536 filed Oct. 24, 1983 and now abandoned.

BACKGROUND OF THE INVENTION (1) Field of the Invention

The present invention relates to a process for producing an ether compound by the so-called ether exchange reaction, in which a different ether compound from the desired ether compound is reacted with a hydroxy group containing compound in the presence of a heteropoly acid or an acidic salt thereof as the catalyst.

(2) Description of the Prior Art

Conventionally, ether compounds have been produced by the following processes;
  (a) Intermolecular dehydration process between same or different hydroxy group containing compounds.
  (b) So-called Williamson reaction process in which a halogenated hydrocarbon is reacted with a hydroxy group containing compound.
  (c) Condensation reaction process of a hydroxy group containing compound with a sulfuric acid ester.
  (d) Addition reaction process of an olefin to a hydroxy group containing compound.
  (e) Addition reaction process of an alkylene oxide to a hydroxy group containing compound.

These conventional processes can be applied only to specific ether compounds and have been inevitably accompanied with lots of by-products of which the disposal may be troublesome.

Besides these conventional processes, simple processes for producing specific ether compounds such as mono- or polyalkeneneglycol diethers were recently disclosed. (U.S. Pat. Nos. 4,146,436, 4,385,190 and 4,391,994). In these processes, raw materials are lower alkyl ether and alkylene oxide, which naturally can not be accompanied by lots of by-products. But the target of both these direct processes and the conventional process (e) is towards the production of specific ether compounds such as ethers having more than one oxyalkylene group. Moreover, highly reactive alkylene oxide is employed as one of the raw materials and the product is inevitably an ether mixture consisting of one or more insertion or addition products of the alkylene oxide, and optionally, not only the isolation of each ether is desired, but some of them are not always required. In the aforementioned mixture, are mingled by-products scarcely separated out from the mixture.

Another simple process in which ethyleneglycol monoalkyl ether is reacted with dialkyl ether by an ether-exchange reaction to ethyleneglycol dialkyl ether in the presence of the defined cation-exchange resin as the catalyst has been disclosed recently. (U.S. Pat. No. 4,231,413). This ether-exchange process is indeed new, but can not be applied to various kinds of ether compounds and the product is defined. This product is accompanied with a large amount of by-products, such as 1,4-dioxane due to the cyclization reaction of the raw material, ethyleneglycol monoalkyl ether and others due to the decomposition of the catalyst. Moreover, the catalyst is rapidly degraded, its efficient recovery or re-use is impossible, and the selection of reactor materials resistant to the corrosion in this process is very difficult.

SUMMARY OF THE INVENTION

Now it has been discovered that it is possible to produce various kinds or ether compounds industrially and advantageously, and the inventors have made the present invention. Namely, the present invention provides a process for producing an ether compound in which an ether compound different from the desired ether compound is reacted with a hydroxy group containing compound in the presence of a heteropoly acid and/or its acidic salt.

DESCRIPTION OF THE PREFERRED EMBODIMENTS

A heteropoly acid and/or its acidic salt (hereinafter, both are called as heterpoly acids.) employed in the present process generally comprise a hetero atom and a poly atom, and the ratio of the former to the latter is in the range of 1/6 to 1/12. As the hetero atom, boron, silicon, phosphorus, chromium, germanium, titanium, manganese, iron, cobalt, arsenic or others may be rised. And, as the poly atom, which coordinates with the hetero atom via an oxygen atom, molybdenum, tungsten, vanadium, niobium or their mixture may be exemplified. Protons of the above heteropoly acid may be partly substituted by a metal cation, an ammonium cation or an organic ammonium cation, and this substituted salt is the acidic salt of the heteropoly acid. Among these, the metal salt is preferably employed in the present invention. As the metal cation, an ion of an alkali metal, an alkali-earth metal, copper, silver, cobalt, nickel, zinc, cadmium, alminium, tin, manganese or the like may be exemplified.

Among these heteropoly acids, preferable acids having the ratio of the hetero atom to the poly atom, 1:12, are employed in the present invention.

For example, dodecamolybdophosphoric acid, dodecamolybdosilicic acid, dodecamolybdotitanic acid, dodecamolybdoarsenic acid, dodecamolybdogermanic acid, dodecatungstphophoric acid, dodecatungstosilicic acid, dodecatungstoboric acid, dodecatungstotitanic acid, dodecatungstoarsenic acid, dodecatungstoferric acid, dodecatungstocobaltic acid, dodecatungstomolybdophosphoric acid, dodecamolybdovanadosilicic acid, dodecamolybdovanadophosphoric acid, dodecatungstovanadosilicic acid or the like are examples of the heteropoly acids. And dodecamolybdosilicic acid disodium salt, dodecatungstosilicic acid monocalcium salt, dodecamolybdophosphoric acid monocopper salt, dodecamolybdophosphoric acid dimanganese salt of others are examples of acidic salts.

Among these heteropoly acids, acidic salts of monosodium and monomanganese are especially preferable and their hetero atom is selected from the group consisting of boron, silicon, phosphorus, and germanium, and their poly atom is selected from the group consiting of molybdenum and tungsten.

As is known well, the foregoing heteropoly acids may be classified as a protonic acid and, moreover, classified as a strong acid which has no acidity distribution. Besides, they have the capability of oxidation or reduction and some of them may dissolve not only in water but in various organic solvents. From those peculiarities, heteropoly acids may be distinguished from the popular solid acid.

It may be due to above peculiarities that popular strong acids such as sulfuric acid, hydrochloric acid or others, do not display the catalytic effect to the reaction process of the present invention, but these heteropoly acids, in spite of a kind of protonic acid, are able to display remarkably the catalytic effect, of which the detail mechanism now has not become clear. The employment of heteropoly acids in the present reaction is able to bring about the high reactivity of raw materials hereinbefore mentioned, but not to cause practically the formation of such by-products as resinous or carbonized residue. Moreover, heteropoly acids, compared with a cation exchange resin having strong acidity, are so stable against heat that they are able to be circulated effectively even after being subjected to a heated situation such as caused in the distillation of the reaction mixture, and further, after the reaction mixture is neutralized, heteropoly acids are recovered and reactivated with an acid prior to the distillation of the mixture, and heteropoly acids are able to be circulated without the corrosion of reactor material.

As set forth before, heteropoly acid are essential as the catalyst of the present process and they occasionally include the water of crystallization in much quantities besides the water related to the structure formation of the acids themselves. The amount of the crystallization water often affects the catalytic activity of heteropoly acids, but in the present process, the crystallization water does not always affect the catalytic activity and the activity is not decreased in the presence of water other than crystallization water.

One of the raw materials in the present invention is an ether compound having the same or different two hydrocarbon radicals bonded to each other via an oxygen atom and optionally substituted by hetero atoms.

Thus, the raw materials or starting materials have the general formula (I):

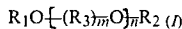

$$R_1O\text{-}\!\!\!+\!\!\!(R_3)_m O\!\!\!+\!\!\!_n R_2 \quad (I)$$

in which $R_1$ and $R_2$ are the same or different hydrocarbon radicals having 1 to 20 carbon atoms and optionally having hetero atoms or hetero atom substituted radicals; $R_3$ is a divalent hydrocarbon radical having 2 to 4 carbon atoms and optionally has hetero atoms or hetero atom substituted radicals; m is a positive integer ranging from 1 to 4; and n is the number of repeating units and is zero or a positive integer ranging from 1 to 8. As $R_1$ and $R_2$, a saturated or unsaturated aliphatic radical, an aryl radical, a cycloaliphatic radical, a heterocyclic radical or the like may be exemplified and these may be substituted partially by a halogen atom, a metal atom, an other hydrocarbon radical or so. The terminal carbon atom of the hydrocarbon radicals may also be substituted by such radical as tertiary ammonium radical, a sulfonium radical, a phosphonium radical, or an amine radical or so.

In explaining the foregoing substituents more precisely, $R_1$ and $R_2$ may be respectively an alkyl radical, an alkenyl radical, a cycloalkyl radical, an aryl radical, a substituted aryl radical or others having 1 to 20 carbon atoms and optionally being substituted by at least one halogen atom, one alkoxy radical, one amino radical, one heterocyclic radical, one mercapto radical, one thioether radical, or one ionic radical heretofore mentioned such as a tertiary ammonium radical. $R_3$ is a divalent hydrocarbon radical such as an ethylene radical, a propylene radical, a butylene radical and optionally they may be substituted by such radicals as mentioned in $R_1$ and $R_2$.

As especially preferable ether compounds of which $R_1$ and $R_2$ are alkyl radicals having 1 to 4 carbon atoms, a dialkylether such as dimethyl ether, diethyl ether, methylethyl ether, di-isopropyl ether, di-n-butyl ether or the like, a mono- or polyalkyleneglycol dialkyl ether such as mono- or polyethyleneglycol dimethyl ether or its diethyl ether or the like may be used, and those are employed as one component or a mixture thereof.

Another raw material in the present invention is a, a hydroxy group containing component which may comprise many compounds known generally as mono- or polyvalent alcohols or as mono- or polyvalent phenols. Generally, in those compounds, at least one hydrogen atom bonded to a carbon atom in the hydrocarbon radical is substituted by a hydroxy radical. And the hydrocarbon radical may be optionally substituted by hetero atoms or hetero atom substituted radicals as mentioned in the description regarding the ether compound. Further, in the compound, derivatives, of which the hydroxy radical is masked by a protective radical are included. As the derivatives, a silyl ether, an aromatic sulfonate, an acetal, a formal or the like may be used.

The hydroxy group containing compound used in the present invention is represented by a general formula (II),

$$R_4\text{---}(OH)_p \quad (II)$$

in which $R_4$ is a mono-, di- or trivalent hydrocarbon radical having 1 to 10 carbon atoms, optionally substituted by at least one hetero atom, but the atom covalently bonded with the hydroxy radical is necessarily a carbon atom and p is 1, 2 or 3.

As the compound having one, two or three hydroxy radicals, a saturated or unsaturated aliphatic alcohol, an alicyclic alcohol, an alcohol having at least one aryl radical, a phenol, a bisphenol or others combined with these may be used.

Among these compounds having the general formula (II), the compound having a general formula (III) is more preferably employed in the present invention,

$$R_5O\text{-}\!\!\!+\!\!\!R_7O_q\!\!\!+\!\!\!R_6 \quad (III)$$

in which both $R_5$ and $R_6$ are hydrogen atoms or one of them is a hydrogen atom and the other is an alkyl radical having 1 to 4 carbon atoms and $R_7$ is alkylene radical having 2 to 4 carbon atoms and q is 0 or a positive integer ranging 1 to 10.

As these compounds, an aliphatic alcohol such as methanol, ethanol, propanol, butanol, an alkyleneglycol such as ethyleneglycol, propyleneglycol, butyleneglycol or polyethyleneglycol, polypropyleneglycol having less than 10 repeating units, a monomethyl or monoethyl ether of above glycols or the like may exemplified, and these may be employed as one component or a mixture thereof.

Prior to the start of the present reaction with two kinds of compounds set forth before, the water content in heteropoly acids catalyst shall be adjusted by a known method. Meanwhile, the employed form of the catalyst may be decided in consideration of the reaction system, the reaction mixture treatment, the recyclization of the catalyst or so, and the catalyst may be employed as it is or in a supported form on silica, alumina, active charcoal. Then, the present reaction may be carried out. As for the present reaction system, any system such as a batch system, continuous system or combined both may be accepted and the vapor phase system or the liquid phase system may be accepted. Further, when the catalyst is employed in the supported form, a fixed-bed reactor may be more available.

In the present reaction, any inert solvent such as dichloromethane, nitromethane, monochlorobenzene, ethylacetate, dioxane or so may be employed, if necessary, for the purpose of dissolving or mixing of the two raw materials and the catalyst, and removing the heat of the reaction. Considering a reaction operation free from danger, the continuance of the catalyst activity or the prevention of an abnormal reaction, the present reaction is preferably carried out under the atmosphere of an inert gas, such as nitrogen or helium.

The following are the reaction conditions in the present invention. The temperature is preferably set in the range of 0° to 300° C. The pressure is determined by the reaction form and generally is adequate up to the self-generated pressure due to the reaction temperature, but occasionally it may be increased with the aid of an inert gas addition. The reaction time is voluntary and may be determined by various factors, such as the variation of raw materials and the catalyst employed, the presence of solvents, the temperature of the pressure set before the reaction and other factors.

The amount of the catalyst, heteropoly acids, charged to the present process is 0.01 to 50 wt% and preferably 0.1 to 20 wt% to a raw material, an aforementioned ether compound. However, when a continuous process with a fixed-bed reactor is used, the reaction may be carried out with the amount adjustment of the ether compound passing through the bed and its amount is to be set in the range of 0.01 to 10 weight parts over a unit time and one weight part of heteropoly acids.

The molar ratio of two raw materials, an ether compound and a hydroxy group containing compound both employed in the present process is usually 1 and optionally either may be employed excessively, for example, in the range of 5 to 10 moles of one material to one mole of the other material.

According to the inventive concept a first ether compound is reacted with a hydroxy containing compound to a second ether compound, different from the starting ether and concurrently a by-product, a different hydroxy group containing compound from the starting compound is produced, which may be separated from the reaction product by any known operation such as distillation, extraction or so, and which may be of course available for any useful purpose different from the present object.

After the present reaction has been completed, each desired ether compound may be isolated by known operations such as rectification prior to or after the separation of the catalyst, heteropoly acids. When the catalyst is not separated from the desired ether compound prior to the isolation, it shall be recovered from the desired ether compound by a known process or operations, and the catalyst recovered from the reaction mixture or the desired ether compound is able to be recycled, if necessary, after the re-activation treatment.

As set forth hereinafter, the present invention discloses the advantageous process in which various kinds of ether compounds are able to be produced from two raw materials by using heteropoly acids as the catalyst, and a great deal of troublesome inorganic salt does not form as a by-product.

For the purpose of giving those skilled in the art a better understanding of the invention, the following Examples and Comparison Example are given, and all parts hereinafter are parts by weight.

EXAMPLE 1

Into a stainless-steel autoclave, 74.1 parts of n-butyl alcohol, 92.1 parts of dimethyl ether and 2 parts of 12-tungstophosphoric acid were charged. After the autoclave was sealed under nitrogen atmosphere, it was heated with agitation to 180° C. and this temperature was maintained for 4 hours. The reaction pressure was raised by heating up to 40 kg/cm$^2$ and finally reached 33 kg/cm$^2$. After 4 more hours reaction, the autoclave was cooled to room temperature and released, then the reaction mixture was poured off to the distillation still. From the still, at first, unreacted dimethyl ether was recovered by the distillation under dry-ice cooling and the residual mixture was analyzed by gas chromatography.

From the result of the analysis, it was found that 62.5% of the charged n-butyl alcohol had been reacted and following products were present in the mixture;

methyl butyl ether—44.1 parts
dibutyl ether—8.2 parts
butene-1*—3.5 parts
*present in recovered dimethyl ether.

The selectivity of methyl butyl ether to reacted n-butyl alcohol was 80.0%.

EXAMPLE 2

Into a similar autoclave as mentioned in Example 1, 76.1 parts of ethyleneglycol monomethyl ether, 92.1 parts of dimethyl ether and 2 parts of 12-molybdophosphoric acid were charged and the autoclave was sealed under nitrogen atmosphere. With agitation, the autoclave was heated to 180° C., this temperature was maintained for 4 hours, and the reaction pressure was rising with heating up to 41 kg/cm$^2$ and finally reached 35 kg/cm$^2$. After the autoclave was cooled to room temperature and released, then unreacted dimethyl ether was recovered by the distillation under dry-ice cooling. By gas chromatographic analysis of the residual mixture, it was found that 78.5% of the charged ethyleneglycol monomethyl ether had been reacted and following products were present in the mixture;

ethyleneglycol dimethyl ether—64.1 parts
diethyleneglycol dimethyl ether—6.6 parts
1,4-dioxane—0.4 parts
diethyleneglycol monomethyl ether—2.4 parts The selectivity of ethyleneglycol dimethyl ether to reacted ethyleneglycol monomethyl ether was 90.7%.

EXAMPLE 3

Into a similar autoclave as mentioned in Example 1, 47.1 parts of phenol, 46.1 parts of dimethyl ether and one part of 12-tungstosilicic acid dihydrate were charged, and the autoclave was sealed under nitrogen atmosphere. With agitation, the autoclave was heated to 170° C., this temperature was maintained for 5 hours, and the reaction pressure was rising up to 38 kg/cm$^2$ and finally reached 31 kg/cm$^2$. After 5 more hours reaction, the autoclave was cooled to room temperature and released, then unreacted dimethyl ether was recovered by the distillation under dry-ice cooling, by gas chromatographic analysis of the residual mixture, it was found that 34.6 parts of methyl phenyl ether was present in the mixture. 65.0% of phenol had been reacted and the selectivity of methyl phenyl ether was 97.0% to reacted phenol.

EXAMPLE 4

Into a similar autoclave as mentioned in Example 1, 45.1 parts of ethyleneglycol monoethyl ether, 74.1 parts of diethyl ether and one part of 12-tungstoboric acid monohydrate were charged, and the autoclave was sealed under the nitrogen atmosphere. With agitation, the autoclave was heated to 180° C. for 5 hours and the reaction pressure was rising up to 18 kg/cm$^2$ and finally reached 12 kg/cm$^2$. After the autoclave was cooled to room temperature and released, unreacted diethyl ether was removed by distillation from the reaction mixture. By gas chromatographic analysis of the residual mixture, it was found that;
  ethyleneglycol diethyl ether—41.3 parts
  diethyleneglycol diethyl ether—4.9 parts
  1,4-dioxane—0.9 parts
and diethyleneglycol monoethyl ether, 2.7 parts were present.

The selectivity of ethyleneglycol diethyl ether was 86.2% to reacted ethyleneglycol monoethyl ether, and its 82.0% and 38.1% of diethyl ether had been reacted.

EXAMPLES 5 TO 12

Example 1 was repeated with various raw materials and heteropoly acids, all of which and reaction conditions were indicated in Table-1. All these results were indicated in Table-2.

COMPARISON EXAMPLE 1

Example 2 was repeated except that 5.0 parts of Naflon 511 (the trade-name of fluorine containing acidic cation exchange resin produced by E. I. du Pont) was employed as the catalyst. In Table-1, reaction conditions, in Table-2, the result both were indicated.

This result shows clearly, that, when the ion exchange resin was employed as the catalyst, the amount of by-product, 1,4-dioxane was greatly increased and the amount of other by-products due to the decomposition of the catalyst was also increased notably.

TABLE 1

| Example or Comparison Example | Raw material | | | | | | Reaction Condition | | |
|---|---|---|---|---|---|---|---|---|---|
| | Ether compound (parts) | | Hydroxy group containing compound (parts) | | Heteropoly acids (parts) | | Reaction temperature (°C.) | Reaction Time (hours) | Maximum Reaction Pressure (kg/cm$^2$) |
| Example 5 | $CH_3OCH_3$ | 92.1 | $HOCH_2CH_2OH$ | 31.0 | 12-molybdosilicic acid tetrahydrate | 0.8 | 180 | 4 | 41 |
| Example 6 | $(n-C_4H_9)_2O$ | 65.1 | $n-C_4H_9OCH_2CH_2OH$ | 29.6 | 12-tungstophosphoric acid dihydrate | 0.5 | 180 | 4 | 5 |
| Example 7 | $C_2H_5OC_2H_5$ | 74.1 | $n-C_7H_{15}OH$ | 58.1 | 12-tungstosilicic acid monohydrate | 1.0 | 170 | 4 | 18 |
| Example 8 | $C_2H_5OC_2H_5$ | 74.1 | $C_2H_5O(CH_2)_4OH$ | 59.0 | 12-tungstogermanic acid dihydrate | 1.0 | 180 | 4 | 19 |
| Example 9 | $C_2H_5OC_2H_5$ | 74.1 | $CH_3$—⟨O⟩—OH | 54.1 | 12-molybdotitanic acid tetrahydrate | 1.0 | 180 | 4 | 17 |
| Example 10 | $CH_3OCH_2OCH_3$ | 76.1 | $n-C_4H_9OH$ | 37.1 | 12-molybdoarsenic acid monohydrate | 0.5 | 130 | 1 | 10 |
| Example 11 | $CH_3OCH_3$ | 92.1 | $CH_3OCH_2CH_2OH$ | 76.1 | 12-tungstosilic acid monosodium salt | 0.1 | 180 | 5 | 38 |
| Example 12 | $C_2H_5OC_2H_5$ | 74.1 | ⟨O⟩—OH | 47.1 | 12-tungstophosphoric acid monomanganese salt | 0.1 | 180 | 5 | 18 |
| Comparison Example 1 | $CH_3OCH_3$ | 92.1 | $CH_3OCH_2CH_2OH$ | 76.1 | Nafion 511* | | 180 | 6 | 20 |

*tradename of the cation exchange resin produced by E. I. du Pont

TABLE 2

| Example or Comparison Example | Reaction Product | | | |
|---|---|---|---|---|
| | Structure and selectivity (%) to hydroxy group containing compound used | | | |
| Example 5 | $CH_3OCH_2CH_2OH$ 72.7 | $CH_3OCH_2CH_2OCH_3$ 15.0 | $HO(CH_2CH_2O)_2H$ 7.6 | $CH_3O(CH_2CH_2O)_2H$ 4.3 |
| Example 6 | $n-C_4H_9OCH_2CH_2O(n-C_4H_9)$ 77.5 | $n-C_4H_9O(CH_2CH_2O)_2-(n-C_4H_9)$ 13.7 | $n-C_4H_9O(CH_2CH_2O)_2OH$ 5.2 | 1,4-dioxane 2.5 |
| Example 7 | $n-C_7H_{15}OC_2H_5$ 71.8 | $n-C_7H_{15}O(n-C_7H_{15})$ 28.0 | | |
| Example 8 | $C_2H_5O(CH_2)_4OC_2H_5$ 81.3 | $C_2H_5(CH_2)_4O(CH_2)_4OC_2H_5$ 13.0 | $C_2H_5O(CH_2)_4O(CH_2)_4OH$ 4.8 | |

TABLE 2-continued

| Example or Comparison Example | Reaction Product Structure and selectivity (%) to hydroxy group containing compound used | | | |
|---|---|---|---|---|
| Example 9 |  96.5 | | | |
| Example 10 | n-C$_4$H$_9$OCH$_3$ 68.0 | n-C$_4$H$_9$OCH$_2$OCH$_3$ 30.1 | | |
| Example 11 | CH$_3$OCH$_2$CH$_2$OCH$_3$ 88.2 | CH$_3$(OCH$_2$CH$_2$)$_2$OCH$_3$ 8.0 | CH$_3$O(CH$_2$CH$_2$O)$_2$H 3.0 | 1,4-dioxane 0.8 |
| Example 12 |  95.9 | | | |
| Comparison Example 1 | CH$_3$OCH$_2$CH$_2$OCH$_3$ 60.7 | CH$_3$(OCH$_2$CH$_2$)$_2$OCH$_3$ 9.0 | 1,4-dioxane 19.8 | other by-products 10.5 |

What is claimed is:

1. A process for producing a desired ether compound by an ether exchange reaction, said process comprising: reacting a starting ether compound having the general formula (I)

$$R_1O[(R_3)_{\overline{m}}O]_{\overline{n}}R_2 \quad (I)$$

with a hydroxy-group-containing compound having the general formula (II)

$$R_4(OH)_p \quad (II)$$

in which R$_1$ and R$_2$ are the same or different hydrocarbon radicals each having from 1 to 20 carbon atoms or the same or different hydrocarbon radicals each having from 1 to 20 carbon atoms and substituted with oxygen; R$_3$ is a divalent hydrocarbon radical having from 2 to 4 carbon atoms or a divalent hydrocarbon radical having from 2 to 4 carbon atoms substituted with oxygen; R$_4$ is a monovalent, divalent or trivalent hydrocarbon radical having from 1 to 10 carbon atoms or a monovalent, divalent or trivalent hydrocarbon radical having from 1 to 10 carbon atoms and being substituted with an oxygen atom provided the atom covalently bonded with the hydroxy radical is a carbon atom; m is a positive integer ranging from 1 to 4; n is the number of repeating units and is zero or a positive integer ranging from 1 to 8; and p is 1, 2 or 3 in the presence of a catalyst consisting essentially of a heteropoly acid or an acidic salt thereof containing a poly atom coordinated via an oxygen atom with a hetero atom to produce said desired ether compound by said ether exchange reaction, said poly atom being selected from the group consisting of molybdenum, tungsten, vanadium, niobium and mixtures thereof, and said hetero atom being selected from the group consisting of boron, titanium, silicon, germanium, phosphorus, arsenic, chromium, manganese, iron and cobalt.

2. The process according to claim 1, wherein the heteropoly acid or an acidic salt thereof has a ratio of the hetero atom to the poly atom of from 1:6 to 1:12.

3. The process according to claim 1, wherein said heteropoly acid of an acidic salt thereof is an acidic salt selected from the group consisting of dodecatungstocilicic acid monosodium salt and dodecatungstophosphoric acid monomanganese salt.

4. The process according to claim 1, wherein R$_1$ and R$_2$ are the same or different alkyl radicals having from 1 to 4 carbon atoms.

5. The process according to claim 1, wherein the hydroxy-group-containing compound represented by the general formula (II) is a hydroxy-group-containing compound having the general formula (III)

$$R_5O—R_7O)_qR_6 \quad (III)$$

in which at least one of R$_5$ and R$_6$ are hydrogen atoms and when only one of R$_5$ and R$_6$ is a hydrogen atom, then the other is an alkyl radical having 1 to 4 carbon atoms; R$_7$ is an alkylene radical having 2 to 4 carbon atoms; and q is zero or a positive integer ranging from 1 to 10.

* * * * *

UNITED STATES PATENT AND TRADEMARK OFFICE
CERTIFICATE OF CORRECTION

PATENT NO. : 4,579,980
DATED : April 1, 1986
INVENTOR(S) : Kiyoahi Kogoma etal.

It is certified that error appears in the above-identified patent and that said Letters Patent is hereby corrected as shown below:

On the title page item [73] should read -- Nisso Petrochemical Industries Co., Ltd, Tokyo, Japan --.

Signed and Sealed this

Fifth Day of August 1986

[SEAL]

Attest:

DONALD J. QUIGG

Attesting Officer

Commissioner of Patents and Trademarks